United States Patent

Semonsky et al.

[11] 3,966,941

[45] June 29, 1976

[54] COMPOSITION FOR PREVENTING LACTATION OR PREGNANCY IN MAMMALS AND THE METHOD FOR USING THE SAME

[75] Inventors: Miroslav Semonsky; Karel Rezabek; Miroslav Seda, all of Prague, Czechoslovakia

[73] Assignee: Spofa United Pharmaceutical Works, Prague, Czechoslovakia

[22] Filed: Dec. 18, 1972

[21] Appl. No.: 315,838

Related U.S. Application Data

[63] Continuation of Ser. No. 74,906, Sept. 23, 1970, abandoned.

[52] U.S. Cl. .............................. 424/261; 260/285.5
[51] Int. Cl.² ................ A61K 31/48; C07D 457/02
[58] Field of Search .................. 424/261; 260/285.5

[56] References Cited
UNITED STATES PATENTS
3,583,992   6/1971   Hoffmann ........................... 424/281

FOREIGN PATENTS OR APPLICATIONS
1,439,953   1/1965   France ............................. 260/285.5

Primary Examiner—Sam Rosen
Attorney, Agent, or Firm—Murray Schaffer

[57] ABSTRACT

α-D-6-methylergolinyl-8-acetamides of the formula:

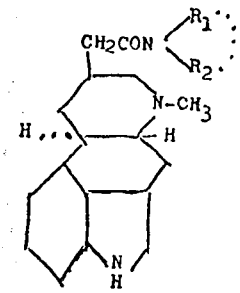

are readily prepared from α-D-6-methylergolinyl-8-acetic acid azide hydrochloride and amines of the formula $R_1$-NH-$R_2$ and may be converted to their salts with inorganic and organic acids by neutralization. In these formulas, $R_1$ may be hydrogen or lower alkyl, $R_2$ may be hydrogen, lower alkyl, cycloalkyl having 5 or 6 carbon atoms, hydroxyalkyl having 3 or 4 carbon atoms, or lower alkoxycarbonylmethyl or $R_1$ and $R_2$ jointly may be divalent alkylene having 4 or 5 C atoms. The salts of most of these bases with physiologically tolerated acids are nontoxic in doses which suppress lactatical and prevent pregnancy in rats when applied orally after copulation. The others, equally non-toxic, extend the effective period of thiopental.

9 Claims, No Drawings

COMPOSITION FOR PREVENTING LACTATION OR PREGNANCY IN MAMMALS AND THE METHOD FOR USING THE SAME

This is a continuation of Ser. No. 74,906, MIROSLAV SEMONSKY ET AL, filed Sept. 23, 1970, now abandoned.

This invention relates to novel derivatives of α-D-6-methylergolinyl-8-acetic acid, and particularly to compounds which are α-D-6-methylergolinyl-8-acetamides or salts of such α-D-6-methylergolinyl-8-acetamides with physiologically tolerated acids.

The basic compounds of the inventor have the formula:

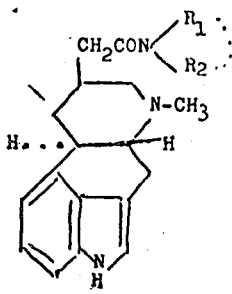

wherein $R_1$ may be hydrogen or alkyl having 1 to 6 carbon atoms, $R_2$ is hydrogen, alkyl having 1 to 6 carbon atoms, cycloalkyl having 5 or 6 carbon atoms, hydroxyalkyl having 3 or 4 carbon atoms, or alkoxycarbonylmethyl having an alkoxy group of 1 to 4 carbon atoms, or $R_1$ and $R_2$ jointly are divalent alkylene having 4 or 5 carbon atoms.

The basic compounds are preferably prepared by reacting α-D-6-methylergolinyl-8-acetic acid azide hydrochloride with an amine of the formula $R_1$-NH-$R_2$, wherein $R_1$ and $R_2$ are as defined above. The bases so obtained are readily neutralized by acids in any conventional manner to form the salts.

It is preferred to react 3 moles of the amine with each mole of the azide hydrochloride and to use an excess of the amine as a diluent, if not more than one of $R_1$,$R_2$ is hydrogen, so that the reaction mixture may consist of as much as 70 moles of the amine permole of the azide hydrochloride. The reaction occurs spontaneously in the mixture at any practical temperature at which the amine is liquid, and may thus be performed at −5°C. to +60°C. It is usually most convenient to operate at room temperature, that is at 15°C. to 25°C. and cooling and heating need not be resorted to unless required to keep the initial reaction mixture in the partly liquid state.

If the reacted amine is costly or not otherwise conventiently available in adequate amounts, it is sufficient to react the azide hydrochloride with at least one mole equivalent to the amine in the presence of at least two mole equivalents of a readily available tertiary amine, such as ethylamine, which neutralizes the hydrochloric acid and hydrogen azide formed by the reaction. The yields, as a rule, are lower than with an excess of the reacted amine.

The amides of the above formula are recovered from the reaction mixture in a conventional manner. Some of the amides of the invention are only sparingly soluble in the reaction mixture and precipitate spontaneously. Those which are soluble may be recovered by diluting the reaction mixture with water, and by extracting the aqueous liquid with an organic solvent not miscible with water in which the base is soluble. The crude compounds obtained by filtration and for extraction of the reaction mixture may be purified by recrystallizing them and/or by passing their solutions over columns of adsorbents which separate the desired product from impurities.

The basic amides form crystalline salts with many inorganic and organic acids, such as hydrochloric, tartaric and maleic acid. The neutral tartrates and the acid maleates are generally quite soluble in water, and their anionic components are non-toxic and without influence on the physiological effects of the cationic amide moiety.

Some amides of the invention have also been prepared by catalytically hydrogenating the double bond in position 9-10 of corresponding α-D-6-methylergolinyl-8-acetamides, but this method requires starting materials which are prepared only in complex procedures and are sensitive to chemical and physical effects of the environment so that they can be purified only with great difficulty, and the yields are low.

The α-D-6-methylergolinyl-8-acetic acid azide hydrochloride employed in the preferred method of this invention is prepared conveniently and in excellent yield by reaction of the corresponding α-substituted acetic acid hydrazide with nitrous acid. Because of the relatively good stability of the starting material, it is used conveniently (M. Semonsky, N. Kucharczyk, Collection Czech. Chem. Commun. 33 1968, 577).

The salts of the amides of the invention with physiologically tolerated acids have strong pharmacological effects regardless of the nature of the anionic moiety, the water soluble salts being most effective.

The neutral tartrate of α-D-6-methylergolinyl-8-acetamide suppresses lactation in rats. Groups of five Wister rats having an average weight of 250g and their litters were investigated. Five days after birth, each litter was reduced to eight normal and healthy animals. The adult females were given seven single daily doses of the tested compound. The weight gain and survival rate of the sucking rats were recorded and the amount of milk ingested was estimated from the size of a white spot visible through the abdominal wall. The young rats surviving the seven-day period were observed for five additional days. A control group did not receive the test compound. A daily dosage of 1 mg of the compound was sufficient for completely suppressing lactation of the adult females, and for causing death of all young animal during the test period due to malnutrition. No comparable effects wereobserved in the control group.

Therapeutically effective dosages will be obvious to those skilled in the art, taking into account weight, age and other similar factors, oral or intravenous dosing, and whether the composition is to be used as an inhibitor for lactation or an inhibitor for pregnancy. Those skilled in the art will fully understand the level of dosages necessary for therapeutic effectiveness.

The same compound we applied orally through a catheter to a group of seven female rats (average weight 200g) on five of seven days starting on the first day after copulation. A single daily dosage of 10 micrograms per animal was found sufficient completely to prevent gravidity in the tested animals. Normal gravidities occurred in a comparable control group.

The toxicity of the tested compound ($LD_{50}$) in mice was 93 mg/kg for intravenous application and more than 1 g/kg for oral ingestion.

Except as stated below, the other compounds of the invention had similar effects. The neutral tartrate of α-D-6-methylergolinyl-8-N-cyclopentylacetamide completely prevented gravidity in rats after a single daily oral dosage of 0.5 mg per animal, and the acid maleate of the corresponding N-diethylamide was similarly effective after a single daily dose of 1 mg per animal.

The neutral tartrate of α-D-6-methylergolinyl-8-N-(+)-1-hydroxy-2-butylacetamide had no effect on the gravidities of inseminated rats in a daily oral dosage of 1.5 mg/kg. However, the same amount, when given intravenously, extended the period of anesthesia induced by thiopental.

The following Examples are further illustrative of this invention.

EXAMPLE 1

A solution of 0.808 g sodium nitrite in 11.7 ml water was added to a solution of 3.5 g α-D-6-methylergolinyl-8-acetic acid hydrazide in 120 ml 0.2 N hydrochloric acid at 0°C. Thereafter, 2 ml 0.2 N hydrochloric acid were added, and the precipitated hydrochloride of the azide formed was recovered by suction filtration. The recovered material was mixed with 28 ml concentrated aqueous ammonium hydroxide solution. The mixture was held at 20°C. for 24 hours and was shaken from time to time. It was then diluted with 44 ml water, and filtered with suction.

The recovered crude α-D-6-methylergolinyl-8-acetamide was washed with water and weighed 2.8 g. It was dissoved in 94 ml methanol and purified by passing the solution over a chromatographic column of 20 g silica gel, methanol being used as an eluent. The fractions of the eluate containing the purified compound were identified by thin layer chromatography on silica gel using p-toluenesulfonic acid as a detecting agent. The compounds of the invention react with this reagent and with von Urk's reagent in the manner of ergot alkaloids. When recrystallized from a mixture of benzene and methanol, the pure base had a melting point of 237°C to 239.5°C. $[\alpha]D^{20} - 84°$ (c=0.38, pyridine).

The neutral tartrate of the base was prepared by combining a stoichiometrically equivalent aqueous solution of D-tartaric acid with a solution of the base in ethanol. The precipitate formed could be recrystallized from water. The tartrate, whether recrystallized or not, melted at 177°–181°C., crystallized again upon continued heating, and ultimately melted at 254° – 257°C. (decomp.). The material recrystallized from water contained 6 molecules of crystal water which could be removed by drying at 100°C. and 0.1 Torr. $[\alpha]D^{20}-21.2°$ (c=0.2, water).

EXAMPLE 2

The azide hydrochloride prepared as in Example 1 from 1.5 α-D-6-methylergolinyl-8-acetic acid hydrazide was mixed by shaking at 0°C. with 15 ml ethylamine, and the solution so obtained was kept at the same temperature for four days. It was then poured into 200 ml water, and the mixture was kept overnight at 0°C. The precipitate formed was recovered by suction filtration and washed with water. The filtrate was saturated with sodium chloride, and another crop of crude α-D-6-methylergolinyl-8-N-ethlacetamide was recovered by suction filtration after two hours. The combined yield of the crude compound was 1.2 g.

It was purified by chromatography as described in Example 1, recrystallized from methanol, and dried at 100°C. and 0.2 Torr. The pure compound melted at 198° – 200°C. $[\alpha]D^{20}-74.5°$ (c=0.68, pyridine).

EXAMPLE 3

The azide hydrocholoride prepared as in Example 2 was added to 10 ml n-hexylamine, and the mixture was shaken vigorously until a homogeneous solution was obtained. After standing 60 hours at 20°C., the reaction mixture was poured into a 2:1 mixture of benzene and ethyl ether, and the volatile materials present were evaporated in a vacuum. The viscous residue was extracted with 250 ml water, and the solidified crystalline product was recovered by suction filtration in an amount of 1.1 g.

When recrystallized from acetone, the α-D-6-methylergolinyl-8-N-n-hexylacetamide so obtained melted at 165° – 167°C. $[\alpha]D^{20}-69°$ (c=0.74, pyridine).

EXAMPLE 4

1.9 g α-D-6-methylergolinyl-8-acetic acid hydrazide were converted to the corresponding azide hydrochloride as described in Example 1, and the latter as added to 4 ml cyclopentylamine. The mixture was kept at 20°C. for 24 hours with intermittent shaking, and was then poured into 150 ml water. The crude α-D-6-methylergolinyl-8-N-cyclopentylacetamide so formed was extracted with chloroform and recovered from the extract by evaporation of the solvent in a vacuum.

The residue was dissoved in 20 ml methanol, and the solution was filtered and passed over a column of silica gel as described in Example 1. 1.4 g of the partly purified compound were recovered from the eluate. When recrystallized from a methanol-benzene mixture and thereafter from methanol, the pure compound melts at 196° – 198°C. $[\alpha]_D^{20}-68°$ (c=0.46, pyridine).

Substitution of cyclohexylamine for the lower homolog in the above reaction yielded the expected cyclohexylacetamide derivative having similar physiological properties.

EXAMPLE 5

1.4 g α-D-6-methylergolinyl-8-acetic acid azide hydrochloride was dried over phosphorus pentoxide at 0.5 Torr. and thereafter added in small batches to a mixture of 1.2 ml (+)-2-aminobutanol and 3 ml triethylamine at −10°C. The mixture was kept at 20°C. for 24 hours, diluted with 45 ml water, and stored overnight. The crude precipitate of α-D-6-methylergolinyl-8-N-(+)-1-hydroxy-2-butylamide was filered off with suction and washed with water. It was dissoved in 20 ml of a 5:2 mixture of chloroform and ethanol, and the solution was filtered by passage over a column of 5 g silica gel which was then washed with the same solvent mixture. The solvent was evaporated from the combined filtrated and washings, and the residue was extracted with 5 ml boiling acetone. 10 ml benzene were added, and the mixture was cooled to −5°C. to induce crystallization.

The precipitated purified product was recovered by filtration and washed with benzene. It melted at 217°–221°C. $[\alpha]_D^{20}-82.5°$ (c=0.4, pyridine).

Corresponding end products were obtained from propanolamine and isopropanolamine in analogous reactions.

EXAMPLE 6

The azide hydrochloride prepared from 1.0 g α-D-6-methylergolinyl-8-acetic acid hydrazide by the method of Example 1 was mixed with 2.0 g ethyl aminoacetate hydrochloride and 14 ml triethylamine. The combined materials were ground for ten minutes whereupon 30 ml ether were added, and the mixture was stored for 48 hours at 20°C. The solids present were separated from the liquid by suction filtration, washed with ether and with water, and dried.

The crude α-D-6-methylergolinyl-8-N-ethoxycarbonylmethylmethylacetamine was dissoved in chloroform, and the solution was filtered by passage over a column of 5 g active aluminum oxide (activity III - IV), the column being washed with a mixture of chloroform and acetone. The volatile solvents were evaporated from the combined filtrate and washings, the residue was dissolved in 8 ml warm chloroform, and the warm solution was poured into a mixture of 15 ml benzene and 5 ml hexane. The liquid mixture was stored overnight at −5°C., and the purified compound was recovered by filtration. It melted at 203° − 205°C. $[\alpha]_D^{20}$ −73° (c=0.52, pyridine).

The esters of methanol and butanol with glycine were used in the same reaction to yield the corresponding N-alkoxycarbonylmethyl homologs.

EXAMPLE 7

The azide hydrochloride prepared by the method of Example 1 from 1.4 g of α-D-6-methylergolinyl-8-acetic acid hydrazide was added in small batches and with shaking to 10 ml diethylamine at 0°C. The precipitate formed in the mixture after 48 hours at 20°C. was filtered off with suction and washed with water. 0.92 g α-D-6-methylergolinyl-8-N-diethylacetamide of m.p. 237° − 240°C. were recovered. $[\alpha]_D^{20}$ −80.0° (c=0.4, pyridine). A secondary crop of 0.23 g was recovered from the mother liquor by dilution with water, extraction of the diluted liquid with chloroform, and evaporation of the chloroform from the extract in a vacuum.

The acid maleate of the base was prepared by dissolving stoichiometrically equivalent amounts of maleic acid and of the base in methanol, and crystallizing the salt from the combined solutions. It melts at 168° − 171°C. $[\alpha]_D^{20}$ −35.0° (c=0.4, water).

When operating at low temperatures and in closed vessels, dimethylamine could be used in the above reaction to yield the corresponding N-dimethylacetamide.

EXAMPLE 8

1.5 g α-D-6-methylergolinyl-8-acetic acid hydrazide were converted to the axide hydrochloride as in Example 1. The latter was added batchwise to 10 ml piperidine, and the resulting mixture was shaken until a clear solution was obtained. The latter was stored for 60 hours at 20°C., and the precipitate formed was filtered off with suction and washed with water. 0.9 g crude α-D-6-methylergolinyl-8-acetic acid piperidide was obtained. An additional amount was recovered from the mother liquor diluted with water by extraction with chloroform, and by evaporating the solvent from the extract in a vacuum. When recrystallized from acetone, the compound was pure as determined by its elementary analysis, and melted at 204° − 207°C. $[\alpha]_D^{20}$ −71° (c=0.65 pyridine).

Pyrrolidine, while inconvenient to handle, may be substituted in the above reaction for piperidine to yield an analogous compound not significantly different from that described above.

What is claimed is:

1. A pharmaceutical composition for preventing lactation or pregnancy in mamals comprising "an admixture with a suitable pharmaceutical carrier" a therapeutically effective dosage of a compound consisting essentially of α-D-6-methylergolinyl-8-acetylamides of the formula:

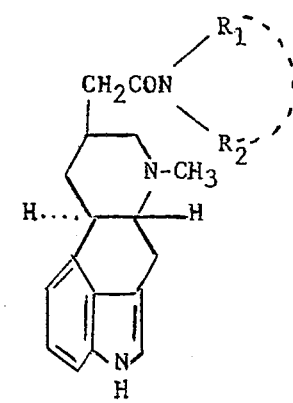

wherein $R_1$ is hydrogen or alkyl having 1 to 6 carbon atoms, $R_2$ is hydrogen, alkyl having 1 to 6 carbon atoms, cycloalkyl having 5 or 6 carbon atoms, hydroxylkyl having 3 or 4 carbon atoms or alkoxycarbonylmethyl having an alkoxy group of 1 to 4 carbon atoms, or $R_1$ and $R_2$ jointly are divalent alkylene having 4 or 5 carbon atoms and pharmaceutically acceptable acid addition salts thereof.

2. A composition of claim 1, wherein $R_1$ and $R_2$ are hydrogen.

3. The composition of claim 2, in the form of its salt with tartaric acid.

4. A composition of claim 1, wherein $R_1$ is cyclopentyl, and $R_2$ is hydrogen.

5. The composition of claim 4, in the form of its salt with tartaric acid.

6. A composition of claim 1, wherein $R_1$ is (+)-1-hydroxy-2-butyl, and $R_2$ is hydrogen.

7. The composition of claim 6, in the form of its salt with tartaric acid.

8. Method of supressing lactation in mammals which comprises administering to a female mammal a therapeutically effective amount of a composition according to claim 1.

9. Method of preventing pregnancy in mammals which comprises administering to a female mammal shortly after copulation a therapeutically effective amount of a composition according to claim 1.

* * * * *